US010274454B2

(12) United States Patent
Nakayama et al.

(10) Patent No.: US 10,274,454 B2
(45) Date of Patent: Apr. 30, 2019

(54) CONCENTRATION MEASUREMENT METHOD, CONCENTRATION MEASUREMENT PROGRAM, CONCENTRATION MEASUREMENT SYSTEM, AND CONCENTRATION MEASUREMENT DEVICE

(71) Applicants: HORIBA, Ltd., Kyoto-shi, Kyoto (JP); HORIBA Advanced Techno, Co., Ltd., Kyoto-shi, Kyoto (JP)

(72) Inventors: Akio Nakayama, Tokyo (JP); Rumiko Furuya, Tokyo (JP); Yuichi Ito, Kyoto (JP); Akio Ishii, Kyoto (JP); Yuji Gyoten, Kyoto (JP); Yoshitake Ando, Kyoto (JP); Hiroaki Murakami, Kyoto (JP)

(73) Assignees: HORIBA, LTD., Kyoto-Shi, Kyoto (JP); HORIBA ADVANCED TECHNO, CO., LTD., Kyoto-Shi, Kyoto (JP)

( * ) Notice: Subject to any disclaimer, the term of this patent is extended or adjusted under 35 U.S.C. 154(b) by 123 days.

(21) Appl. No.: 15/432,240

(22) Filed: Feb. 14, 2017

(65) Prior Publication Data
US 2017/0234826 A1 Aug. 17, 2017

(30) Foreign Application Priority Data
Feb. 15, 2016 (JP) .................................. 2016-025827

(51) Int. Cl.
*G01N 27/416* (2006.01)
*G01N 27/333* (2006.01)
(Continued)

(52) U.S. Cl.
CPC .......... *G01N 27/333* (2013.01); *C02F 3/006* (2013.01); *C02F 3/12* (2013.01); *G01N 27/4163* (2013.01);
(Continued)

(58) Field of Classification Search
CPC ................ G06F 19/70; G01N 33/0006; G01N 27/3274; G01N 27/4175; G01N 27/4163
See application file for complete search history.

(56) References Cited

U.S. PATENT DOCUMENTS 7,943,391 B1 * 5/2011 Byrne .................. G01N 21/274
436/163
2013/0098780 A1 * 4/2013 Georgiou ........... G01N 27/4145
205/792

FOREIGN PATENT DOCUMENTS

JP 2014041109 A 3/2014

OTHER PUBLICATIONS

Easley et al., "Spectrophotometric Calibration of PH Electrodes in Seawater Using Purified m-Cresol Purple," Environmental Science & Technology, 2012, 46, 5018-5024. (Year: 2012).*

* cited by examiner

Primary Examiner — Alexander S Noguerola
(74) Attorney, Agent, or Firm — Alleman Hall Creasman & Tuttle LLP

(57) ABSTRACT

To measure target component concentration in a liquid with higher accuracy without any dedicated apparatus or skill, a method is adapted to include: receiving a successive measurement value obtained by performing successive measurement of the target component concentration with use of a first measurement device immersed in the liquid; receiving a batch measurement value obtained by, with use of a second measurement device, performing batch measurement of the target component concentration in a part sampled from the
(Continued)

liquid; and, when the batch measurement value is received, successively calculating a correlation value indicating the correlation between multiple successive measurement values and multiple batch measurement values respectively obtained in mutually corresponding multiple times of successive measurement and multiple times of batch measurement. In addition, the first measurement device is adapted to calculate the target component concentration or correct a successive measurement value with use of the latest correlation value.

8 Claims, 16 Drawing Sheets

(51) Int. Cl.
| | |
|---|---|
| *C02F 3/00* | (2006.01) |
| *C02F 3/12* | (2006.01) |
| *G01N 33/18* | (2006.01) |
| G06F 19/00 | (2018.01) |
| G01N 27/327 | (2006.01) |
| C02F 101/16 | (2006.01) |

(52) U.S. Cl.
CPC ...... *G01N 33/1813* (2013.01); *C02F 2101/16* (2013.01); *C02F 2209/005* (2013.01); *C02F 2209/006* (2013.01); *C02F 2209/14* (2013.01); *G01N 27/3274* (2013.01); *G06F 19/70* (2013.01)

| | FIRST DAY | SECOND DAY | THIRD DAY | FOURTH DAY | FIFTH DAY | SIXTH DAY | SEVENTH DAY |
|---|---|---|---|---|---|---|---|
| TEMPORARY DATA | ○ | ○ | ○ | ○ | × | × | × |
| TEMPORARY DATA | ○ | ○ | ○ | ○ | ○ | × | × |
| TEMPORARY DATA | ○ | ○ | ○ | ○ | ○ | ○ | × |
| FIRST DAY | ○ | ○ | ○ | ○ | ○ | ○ | ○ |
| SECOND DAY | | ○ | ○ | ○ | ○ | ○ | ○ |
| THIRD DAY | | | ○ | ○ | ○ | ○ | ○ |
| FOURTH DAY | | | | ○ | ○ | ○ | ○ |
| FIFTH DAY | | | | | ○ | ○ | ○ |
| SIXTH DAY | | | | | | ○ | ○ |
| SEVENTH DAY | | | | | | | ○ |

PIECES OF DATA USED TO CALCULATE CORRELATION VALUE

FIG. 12

CONCENTRATION MEASUREMENT METHOD, CONCENTRATION MEASUREMENT PROGRAM, CONCENTRATION MEASUREMENT SYSTEM, AND CONCENTRATION MEASUREMENT DEVICE

TECHNICAL FIELD

The present invention relates to a concentration measurement method, concentration measurement program, concentration measurement system, and concentration measurement device adapted to measure target component concentration in a liquid.

BACKGROUND ART

Treatment such as sewage treatment includes a process of reducing the concentration of a target component in swage water, such as ammonia nitrogen, to a predetermined concentration or less in a biological reactor. In such a process, in order to activate microorganisms, air is sent into the reactor using a blower or the like.

When doing this, if air is continued to be sent even though the concentration of the target component is the predetermined concentration or less, wasted power consumption occurs, and therefore usually, the blower is controlled while successively measuring and monitoring the concentration of the target component contained in the sewage water in the reactor.

As a measurement device used for such successive measurement, for example, as described in Patent Literature 1, one capable of performing successive measurement in a state of being immersed in a reactor without using any reagent, i.e., one using a so-called ion electrode method is suitable.

In such a measurement device, in order to secure measurement accuracy, calibration using a calibration liquid is performed. However, when the calibration liquid itself is a dangerous one or an unstable one, such as a calibration liquid used for ORP measurement or residual chlorine measurement, the problem of the difficulty to prepare the calibration liquid occurs.

Also, when as the measurement device, using a device affected by the interference due to a component (an interfering component) other than the target component, such as a device using an ion electrode method, the effect of the interference due to the interfering component is changed depending on the time-dependent state of a sample, and therefore even when performing the calibration using a calibration liquid, the measurement accuracy is not necessarily high.

CITATION LIST

Patent Literature

Patent Literature 1: JP-A 2014-041109

SUMMARY OF INVENTION

Technical Problem

As a method for securing measurement accuracy when calibration using a calibration liquid is difficult or when using a measurement device affected by the interference due to an interfering component, calibration (sample liquid calibration) adapted to sample a part of a sample under successive measurement, measure the concentration of a target component contained in the sampled sample by another method capable of highly accurately measuring the concentration, and match a measurement value obtained by the measurement device with a measurement value obtained by the highly accurate measurement by that method is conceivable.

Meanwhile, the power consumption of a blower is extremely large, and therefore it is expected in the future that in order to further reduce wasted power consumption of the blower for energy saving, target component concentration is required to be measured with higher accuracy than before.

However, when attempting to match measurement values with each other at multiple concentrations in order to improve measurement accuracy in the above-described sample liquid calibration, it is necessary to use sampled sample liquids to prepare calibration liquids of the multiple concentrations, which requires dedicated apparatuses and dedicated skills and also takes time and effort as a daily routine, and when a calibration frequency decreases, it becomes difficult to secure the measurement accuracy.

Therefore, the present invention is made in order to solve the above-described problems at once, and a main intended object thereof is to, even when calibration using a calibration liquid is difficult or when using a measurement device affected by the interference due to an interfering component, make it possible to measure target component concentration in a liquid with higher accuracy than before.

Solution to Problem

That is, a concentration measurement method according to the present invention is a method for measuring target component concentration in a liquid, and the method includes: a first reception step of receiving a successive measurement value obtained by performing successive measurement of the target component concentration with use of a first measurement device of which a sensor part is immersed in the liquid; a second reception step of receiving a batch measurement value obtained by, with use of a second measurement device different from the first measurement device, performing batch measurement of the target component concentration in a part sampled from the liquid; and a correlation value calculation step of, when in the second reception step, a batch measurement value is received, successively calculating a correlation value indicating the correlation between multiple successive measurement values and multiple batch measurement values respectively obtained in mutually corresponding multiple times of successive measurement and multiple times of batch measurement. In addition, the first measurement device calculates the target component concentration with use of the correlation value or corrects a successive measurement value with use of the correlation value.

In such a concentration measurement method, since the target component concentration is calculated or a successive measurement value is corrected with use of the correlation value between the multiple successive measurement values and the multiple batch measurement values respectively obtained in the mutually corresponding multiple times of successive measurement and multiple times of batch measurement, as long as a value close to a true value obtained by, for example, manual analysis or the like performed for daily management is used as a batch measurement value, successive measurement values can be matched with batch measurement values close to true values at multiple points.

In doing so, even when calibration using a calibration liquid is difficult, or when using a measurement device affected by the interference due to an interfering component, the target component concentration in the liquid can be measured with higher accuracy than before without any dedicated apparatus or dedicated skill. Note that as the manual analysis, an analysis method using, for example, ion chromatography, color reaction, or the like, which is not suitable for successive measurement but enables highly accurate analysis, can be cited.

Also, since the need for dedicated apparatuses and dedicated skills can be eliminated, when in the second reception step, a batch measurement value is received, a correlation value can be successively calculated, and by making the first measurement device calculate the target component concentration or correct a successive measurement value with use of the correlation value, highly accurate measurement can be performed using an appropriate correlation value on a time-dependent basis.

It is preferable that the concentration measurement method further includes: a successive measurement value storage step of storing a successive measurement value received in the first reception step; and a batch measurement value storage step of storing a batch measurement value received in the second reception step. In addition, it is also preferable that in the correlation value calculation step, a correlation value is calculated on the basis of, among stored batch measurement values, multiple batch measurement values obtained during a period from batch measurement performed a predetermined number of times before the latest batch measurement to the latest measurement, and successive measurement values obtained in multiple times of successive measurement respectively corresponding to that multiple times of batch measurement.

Since such a method calculates a correlation value on the basis of multiple successive measurement values and multiple batch measurement values, and therefore a more appropriate value can be obtained as the correlation value.

Also, a concentration measurement program according to the present invention is a program used to measure target component concentration in a liquid, and the concentration measurement program instructs a computer to fulfill functions as: a first reception part adapted to receive a successive measurement value obtained by performing successive measurement of the target component concentration with use of a first measurement device of which a sensor part is immersed in the liquid; a second reception part adapted to receive a batch measurement value obtained by, with use of a second measurement device different from the first measurement device, performing batch measurement of the target component concentration in a part sampled from the liquid; a correlation value calculation part adapted to, when the second reception part receives a batch measurement value, successively calculate a correlation value indicating the correlation between multiple successive measurement values and multiple batch measurement values respectively obtained in mutually corresponding multiple times of successive measurement and multiple times of batch measurement, and a correlation value transmitting part adapted to transmit the correlation value to the first measurement device or a correction part adapted to correct a successive measurement value received by the first reception part with use of the correlation value.

Further, a concentration measurement system according to the present invention is a system that measures target component concentration in a liquid, and the system includes: a first measurement device adapted to perform successive measurement of the target component concentration with a sensor part immersed in the liquid; and an information processing device adapted to transceive data with the first measurement device. In addition, the information processing device has: a first reception part adapted to receive a successive measurement value obtained by performing the successive measurement of the target component concentration with use of the first measurement device; a second reception part adapted to receive a batch measurement value obtained by, with use of a second measurement device different from the first measurement device, performing batch measurement of the target component concentration in a part sampled from the liquid; a correlation value calculation part adapted to, when the second reception part receives the batch measurement value, successively calculate a correlation value indicating the correlation between multiple successive measurement values and multiple batch measurement values respectively obtained in mutually corresponding multiple times of successive measurement and multiple times of batch measurement; and a correlation value transmitting part adapted to transmit the correlation value to the first measurement device or a correction part adapted to correct a successive measurement value received by the first reception part with use of the correlation value.

Such a concentration measurement program or concentration measurement system allows obtaining of the same working effect as that of the above-described concentration measurement method.

In addition, since in the above-described concentration measurement system, the information processing device has the correlation value transmitting part adapted to transmit a correlation value to the first measurement device or a correction part adapted to correct a successive measurement value with use of the correlation value, a user can automatically obtain the target component concentration using the correlation value without taking the trouble to input the calculated correlation value to the first measurement device.

Meanwhile, when a measurement device having an ion electrode is used as the first measurement device, and the target component concentration in the liquid reduces, suspended substances (SS) are reduced, and as a result of demanding a target for a biological reaction, for example, microorganisms suspended in the liquid may be attached to the sensor part and/or the like of the first measurement device, and/or decompose a plasticizer inside the sensor. Accordingly, when the suspended substances in the liquid are reduced, the life of the electrode may be shortened.

Such a phenomenon affecting the life of the electrode may occur, for example, when the value of oxidation-reduction potential (ORP) or a dissolved oxygen amount (DO) is high, under the condition that the activity of the microorganisms is high (e.g., the temperature of the liquid is 30° C. to 40° C.), and/or in other cases.

For this reason, in order to sense such abnormality, it is preferable that the information processing device has: an analysis result reception part adapted to acquire an analysis result different from the target component concentration; and an abnormality sensing part adapted to sense the abnormality of the first measurement device on the basis of the analysis result.

It is preferable that the information processing device further has a maintenance informing part adapted to acquire the correlation value, or the successive measurement values and the batch measurement values as well as on the basis of the correlation value, or the successive measurement values and the batch measurement values, outputting an informing signal prompting maintenance of the first measurement device.

Such a configuration makes it possible to automatically inform a user that the first measurement device needs maintenance or maintenance time is approaching.

In order to make it possible to accurately obtain the correlation value even when the number of data points respectively given by successive measurement values and corresponding batch measurement values is small, such as immediately after the start of system operation or immediately after calibration, it is preferable that the correlation value calculation part calculates the correlation value with additional use of a preliminarily inputted temporary batch measurement value and a temporary successive measurement value preliminarily inputted as a successive measurement value corresponding to the temporary batch measurement value.

Although detailed data will be described later, the above-described configuration makes it possible to accurately obtain the correlation value even when the number of data points respectively given by successive measurement values and corresponding batch measurement values is small, and by correcting a successive measurement value using the correlation value, a successive measurement value can be highly accurately measured.

Also, a concentration measurement device according to the present invention is a concentration measurement device that performs successive measurement of target component concentration in a liquid with a sensor part immersed in the liquid, and the concentration measurement device has: a reception part adapted to receive a batch measurement value obtained by, with use of a second measurement device different from the concentration measurement device, performing batch measurement of the target component concentration in a part sampled from the liquid; a correlation value calculation part adapted to, when the reception part receives the batch measurement value, successively calculate a correlation value indicating the correlation between multiple successive measurement values and multiple batch measurement values respectively obtained in mutually corresponding multiple times of successive measurement and multiple times of batch measurement; and a concentration calculation part adapted to calculate the target component concentration with use of the correlation value.

Such a configuration makes it possible to make the concentration measurement device automatically calculate the correlation value between successive measurement values and batch measurement values as well as calculating the target component concentration with use of the correlation value even without using an information processing device.

Advantageous Effects of Invention

According to the present invention configured as described above, target component concentration in a liquid can be measured with higher accuracy than before without the need for any dedicated apparatus or dedicated skill.

BRIEF DESCRIPTION OF DRAWINGS

FIG. 12 is a diagram illustrating the details of an experiment for comparing the concentration measurement system in the same embodiment and the conventional system;

DESCRIPTION OF EMBODIMENTS

First Embodiment

In the following, a first embodiment of a concentration measurement system 100 according to the present invention will be described with reference to drawings.

<Concentration Measurement System>

A concentration measurement system 100 of the present embodiment is a system used to successively monitor the concentration of a target component contained in, for example, wastewater (hereinafter also referred to as a sample liquid) under process in a biological reactor T (e.g., an aeration tank) where a biological reaction process of ammonia nitrogen is performed using microorganisms in a wastewater treatment process. Note that as the biological reactor T, without limitation to the above-described one where the biological reaction process is performed, an aerobic reactor (nitrification reactor), anaerobic reactor (anoxic reactor, denitrification reactor), nitritation reactor, anammox reactor, or the like is also possible.

Figure 1:
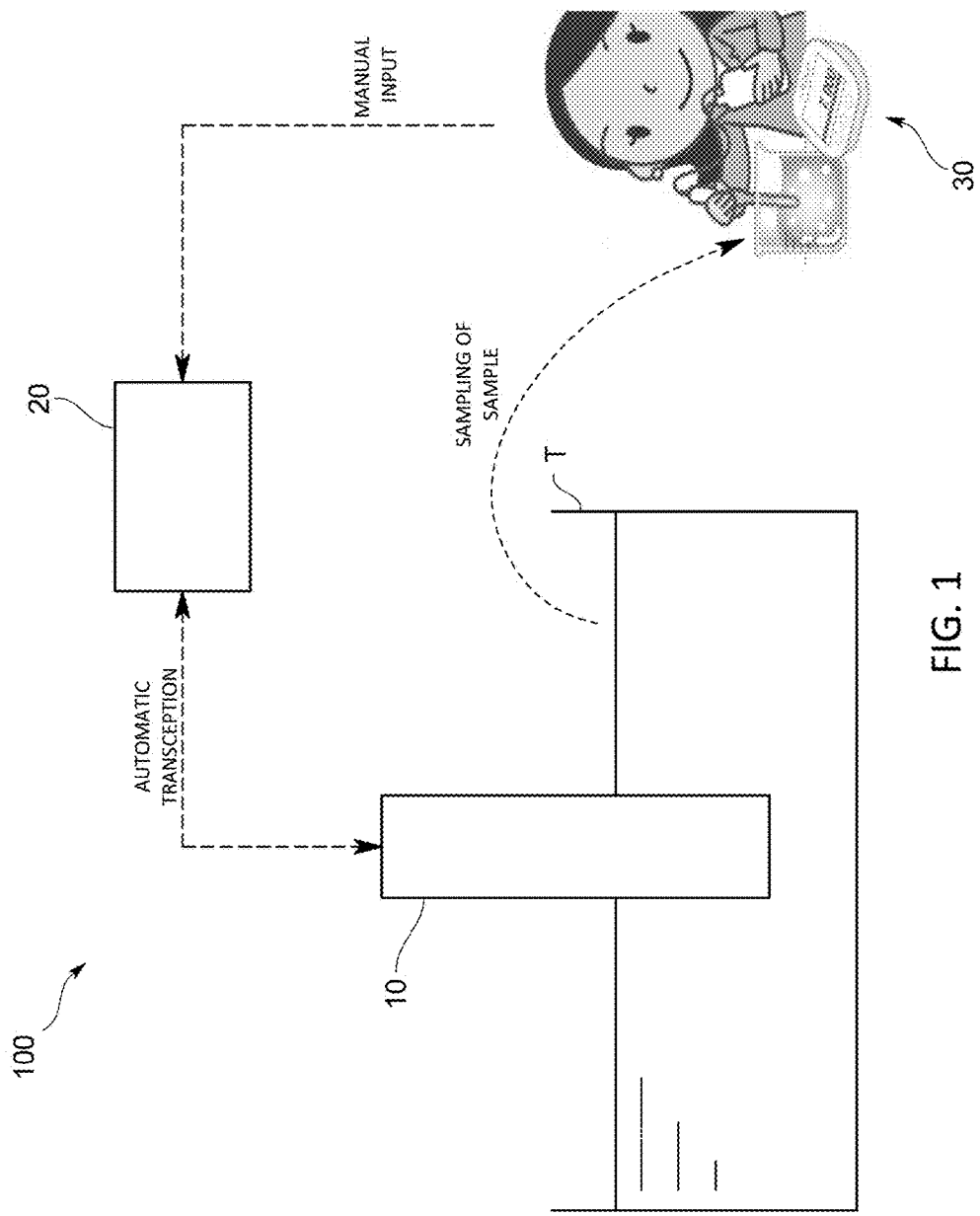
FIG. 1 is an overall configuration diagram schematically illustrating a concentration measurement system in a first embodiment.

Specifically, as illustrated in FIG. 1, the concentration measurement system 100 includes: an ammonia nitrogen meter 10 as a first measurement device adapted to measure the concentration of ammonia nitrogen that is the target component in the sample liquid; and an information processing device 20 adapted to transceive data with the ammonia nitrogen meter 10.

<Ammonia Nitrogen Meter>

The ammonia nitrogen meter 10 is one that as illustrated in FIG. 1, successively measures the concentration of ammonium ions with sensor parts S immersed in the sample liquid as well as outputting the resulting measurement value (hereinafter also referred to as a successive measurement value) to the below-described information processing device 20.

Figure 2:
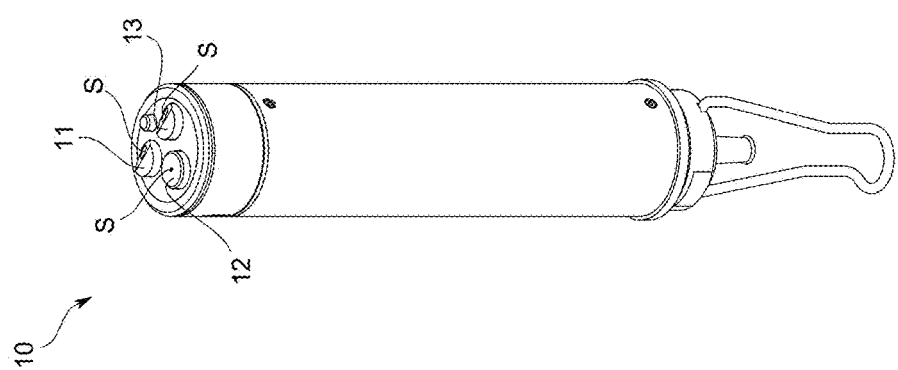
FIG. 2 is a schematic diagram illustrating the configuration of an ammonia nitrogen meter in the same embodiment.

Specifically, the ammonia nitrogen meter 10 is one using an ion electrode method, and as illustrated in FIG. 2, a liquid membrane type ammonia nitrogen meter including: an ammonium ion electrode 11 for measuring a potential due to the ammonium ions; and a reference electrode 12 for measuring a reference potential, in which end parts of the respective electrodes 11 and 12 contacting with the sample liquids are the sensor parts S.

An internal liquid of the ammonium ion electrode 11 contains ammonium chloride, and as an internal electrode, an Ag/AgCl electrode is used. Also, as a responsive membrane, a membrane selectively responding to ammonium ions is used.

The ammonium ion electrode 11 of a liquid membrane type also has the sensitivity to so-called interfering ions other than ammonium ions, and therefore the ammonia nitrogen meter 10 of the present embodiment further includes a potassium ion electrode 13 for measuring a potential due to potassium ions as major interfering ions, and is thereby adapted to be able to correct the interference due to potassium ions in ammonium ions. Note that the sensor part S of the potassium ion electrode 13 is an end part contacting with the sample liquid.

Figure 3:
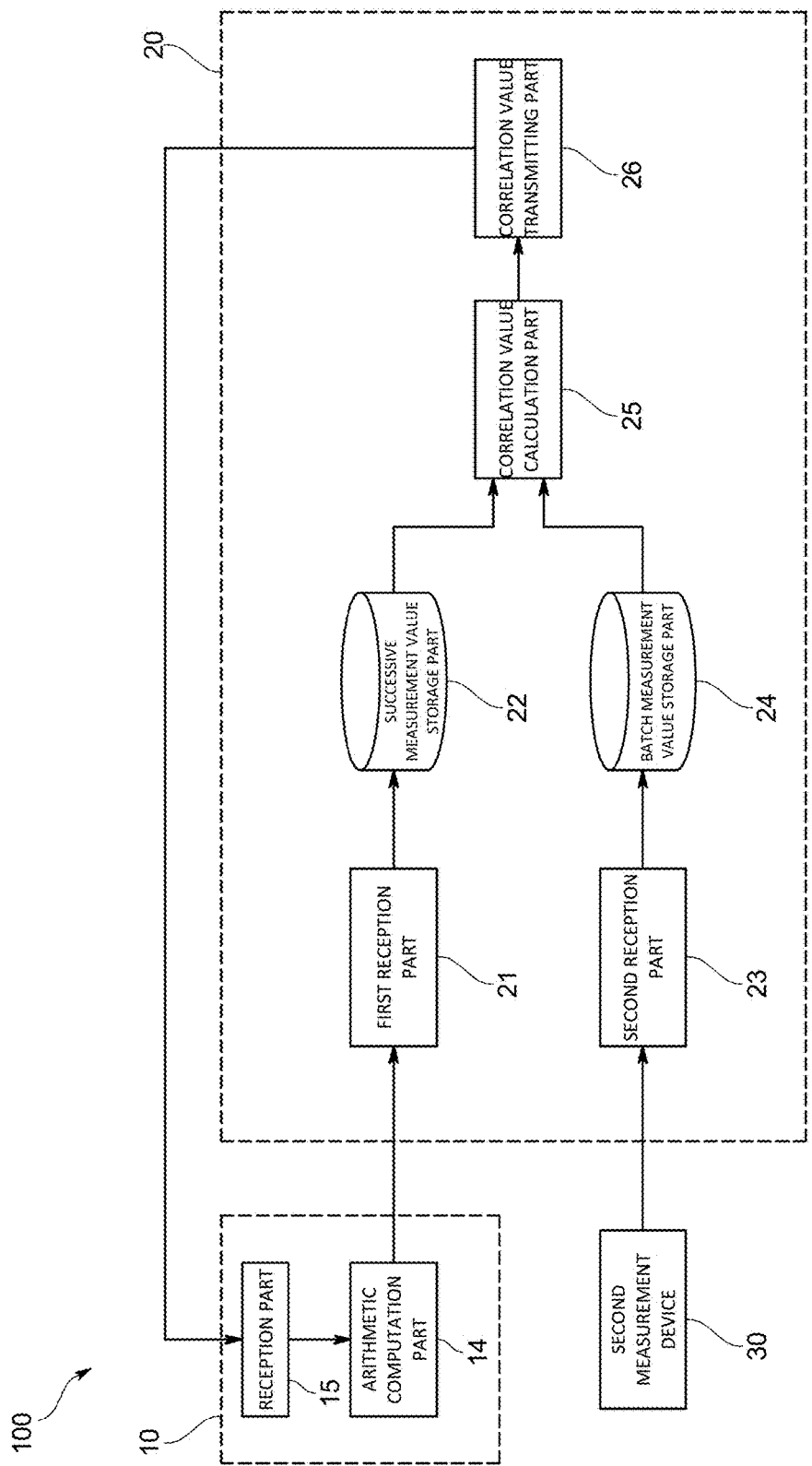
FIG. 3 is a functional block diagram illustrating the functions of an information processing device in the same embodiment.

As illustrated in FIG. 3, the ammonia nitrogen meter 10 includes an arithmetic computation device (not illustrated) that fulfills a function as an arithmetic computation part 14 adapted to compute the concentration of ammonium ions on the basis of the potential difference between the ammonium ion electrode 11 and the reference electrode 12, and outputs a value obtained by the computation in the arithmetic computation part 14 to the information processing device 20 as the successive measurement value.

<Information Processing Device>

The information processing device 20 is a general-purpose or dedicated computer including a CPU, memory, input means, communication interface, display, and the like. In addition, the CPU and its peripheral devices cooperate in accordance with a program stored in a predetermined area of the memory, and thereby as illustrated in FIG. 3, the information processing device 20 is configured to fulfill functions as a first reception part 21, successive measurement value storage part 22, second reception part 23, batch measurement value storage part 24, correlation value calculation part 25, and correlation value transmitting part 26.

Figure 4:
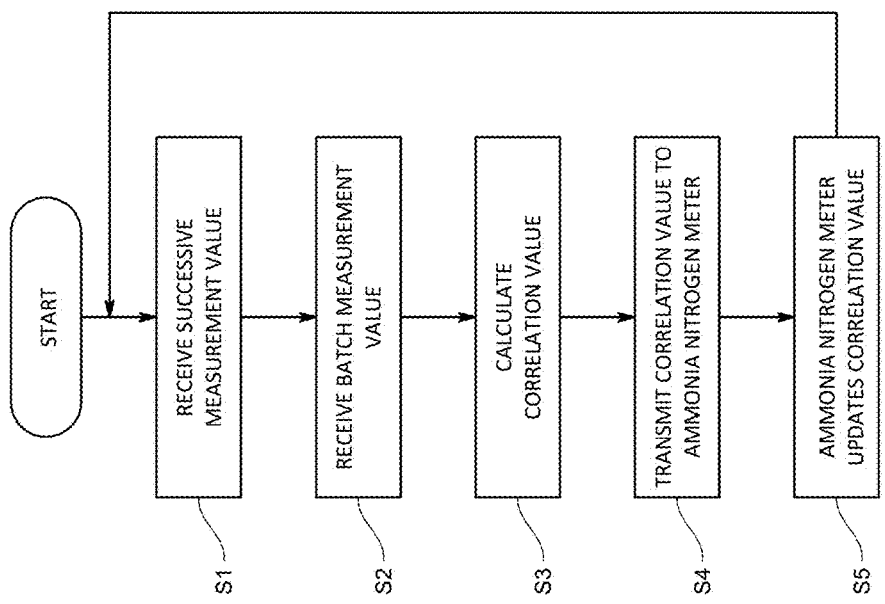
FIG. 4 is a flowchart illustrating the actions of the concentration measurement system in the same embodiment.

In the following, with reference to FIG. 3 and a flowchart of FIG. 4, the actions of the concentration measurement system 100 of the present embodiment will be described while describing the respective parts 21 to 26.

First, when the ammonia nitrogen meter 10 starts to perform successive measurement, the first reception part 21 receives a successive measurement value outputted from the arithmetic computation part 14 of the ammonia nitrogen meter 10 (S1).

The successive measurement value received by the first reception part 21 is sent to the successive measurement value storage part 22 formed in a predetermined area of the memory, and the successive measurement value storage part 22 stores the successive measurement value in chronological order.

Specifically, the successive measurement value storage part 22 stores the successive measurement value received by the first reception part 21 and measurement time when the successive measurement value was measured by the ammonia nitrogen meter 10 (i.e., time when the arithmetic computation part 14 computed the successive measurement value) in connection with each other.

The present embodiment is adapted such that, as illustrated in FIG. 1, in the middle of the above-described successive measurement, a user uses a second measurement device 30 different from the ammonia nitrogen meter 10 to perform batch measurement of the concentration of ammonia nitrogen (the concentration of ammonium ions) contained in the sample liquid sampled from the biological reactor T, and inputs the resulting measurement value (hereinafter also referred to as a batch measurement value) to the information processing device 20.

Describing this more specifically, for example, sewage treatment or the like is generally managed by daily performing batch measurement of the concentration of a target component contained in a sample liquid. For this reason, separately from the above-described successive measurement, for example, the user samples the sample liquid from biological reactor T to manually analyze the concentration of the target component in the sample liquid. In this batch measurement, the user analyzes the concentration of the target component contained in the sample liquid itself sampled from the biological reactor T (i.e., the sample liquid in a state of being sampled), and the sampled sample liquid is analyzed without being subjected to a process such as concentration adjustment.

The present embodiment is adapted to set a measurement device used for the batch measurement as the second measurement device 30, and specifically, the second measurement device 30 is one of a diaphragm type. Also, the second measurement device 30 is one that is not suitable for successive measurement because it requires a reagent but capable of measurement with higher accuracy than the ammonia nitrogen meter 10.

The batch measurement value obtained by the second measurement device 30 is manually inputted to the information processing device 20 by the user using the input means, and the second reception part 23 of the information processing device 20 receives the batch measurement value (S2).

Note that the batch measurement value may be adapted to be inputted from the second measurement device 30 to the information processing device 20 by wire or wireless.

The batch measurement value received by the second reception part 23 is sent to the batch measurement value storage part 24 formed in a predetermined area of the memory, and the batch measurement value storage part 24 stores the batch measurement value in chronological order.

Specifically, the batch measurement value storage part 24 stores the batch measurement value received by the second reception part 23 and sampling time when the sample liquid as a measurement target for the batch measurement value was sampled from the biological reactor T in connection with each other. Note that the sampling time may be inputted to the information processing device 20 by the user using the input means or preliminarily stored in the batch measurement value storage part 24 as batch measurement schedule information.

Then, in the present embodiment, the correlation value calculation part 25 calculates a correlation value indicating the correlation between a successive measurement value and a batch measurement value respectively obtained in mutually corresponding successive measurement and batch measurement (S3).

As used herein, the term "mutually corresponding successive measurement and batch measurement" refers to successive measurement and batch measurement satisfying the condition that, if the sample liquid sampled in the batch measurement and the sample liquid measured in the successive measurement are measured by the same measurement device, substantially the same target component concentration is to be obtained.

In the present embodiment, the mutually corresponding successive measurement and batch measurement are ones satisfying the condition that sampling time when the sample liquid was sampled from the biological reactor T in the batch measurement and measurement time in the successive measurement are substantially coincident with each other.

That is, the correlation value calculation part 25 in the present embodiment refers to the successive measurement value storage part 22 and the batch measurement value storage part 24 to calculate the correlation value on the basis of the batch measurement value and the successive measurement value obtained at the measurement time substantially coincident with the sampling time connected to the batch measurement value.

More specifically, the correlation value calculation part 25 is configured to calculate a correlation value on the basis of multiple batch measurement values obtained during a period from batch measurement performed a predetermined number of times before the latest measurement to the latest measurement and multiple successive measurement values obtained in multiple times of successive measurement corresponding to that multiple times of batch measurement. Herein, the correlation value calculation part 25 is adapted to successively calculate a correlation value when the second reception value 23 receives a batch measurement value. Note that as used herein, the meaning of "successively calculate" includes not only the case where every time the second reception part 32 receives a batch measurement value, a correlation value is calculated but also the case where a correlation value is calculated once every multiple times the second reception part 32 receives a batch measurement value, and it is only necessary that a correlation value is adapted to be updated at a frequency necessary to secure the measurement accuracy of the ammonia nitrogen meter 10 as the first measurement device.

Describing this more specifically, when the second reception part 23 receives a batch measurement value, the correlation value calculation part 25 obtains a correlation expression (correlation model) such as a regression line or a calibration curve on the basis of the deviations, ratios, or the like between a predetermined number of (e.g., 20) successive batch measurement values including the batch measurement value and ones before the batch measurement value, and successive measurement values corresponding to the batch measurement values, and calculates the coefficient of the correlation expression (e.g., a regression coefficient) or a value based on the coefficient (e.g., the reciprocal of the regression coefficient) as a correlation value.

The correlation value calculated by the correlation value calculation part 25 as described above is transmitted to the ammonia nitrogen meter 10 by the correlation value transmitting part 26 (S4).

On the other hand, the ammonia nitrogen meter 10 has a reception part 15 adapted to receive a correlation value transmitted from the correlation value transmitting part 26, and the arithmetic computation part 14 uses the correlation value received by the reception part 15 to calculate the concentration of ammonium ions. That is, the ammonia nitrogen meter 10 of the present embodiment successively receives and updates a correlation value transmitted from the correlation value transmitting part 26 (S5), and successively outputs a successive measurement value calculated using the correlation value to the information processing device 20 (S1).

In the concentration measurement system 100 according to the present embodiment configured as described above, successive measurement values obtained by the ammonia nitrogen meter 10 include measurement values covering the range of low concentration to high concentration, and therefore by calculating a correlation value on the basis of multiple successive measurement values and multiple batch measurement values obtained in mutually corresponding multiple times of successive measurement and multiple times of batch measurement, a successive measurement value can be matched with a batch measurement value on any of a low concentration side and a high concentration side.

This makes it possible to, for example, without performing on-site calibration requiring dedicated apparatuses and dedicated skills, measure the concentration of ammonia nitrogen in sewage water subjected to a biological reaction process with higher accuracy than before, and therefore wasted power consumption of a blower can be reduced to save energy.

Meanwhile, as described above, the ammonia nitrogen meter using the ion electrode method has the sensitivity to interfering ions other than ammonium ions, and in the past, sometimes measurement accuracy has been improved by correcting the interference due to potassium ions that are major interfering ions.

However, even when correcting the interference due to the interfering ions as described above, measurement accuracy to be required in the future cannot be satisfied, and in light of this point as well, it can be said that allowing highly accurate measurement by the concentration measurement system 100 according to the present embodiment is a particularly prominent working effect.

Figure 5:
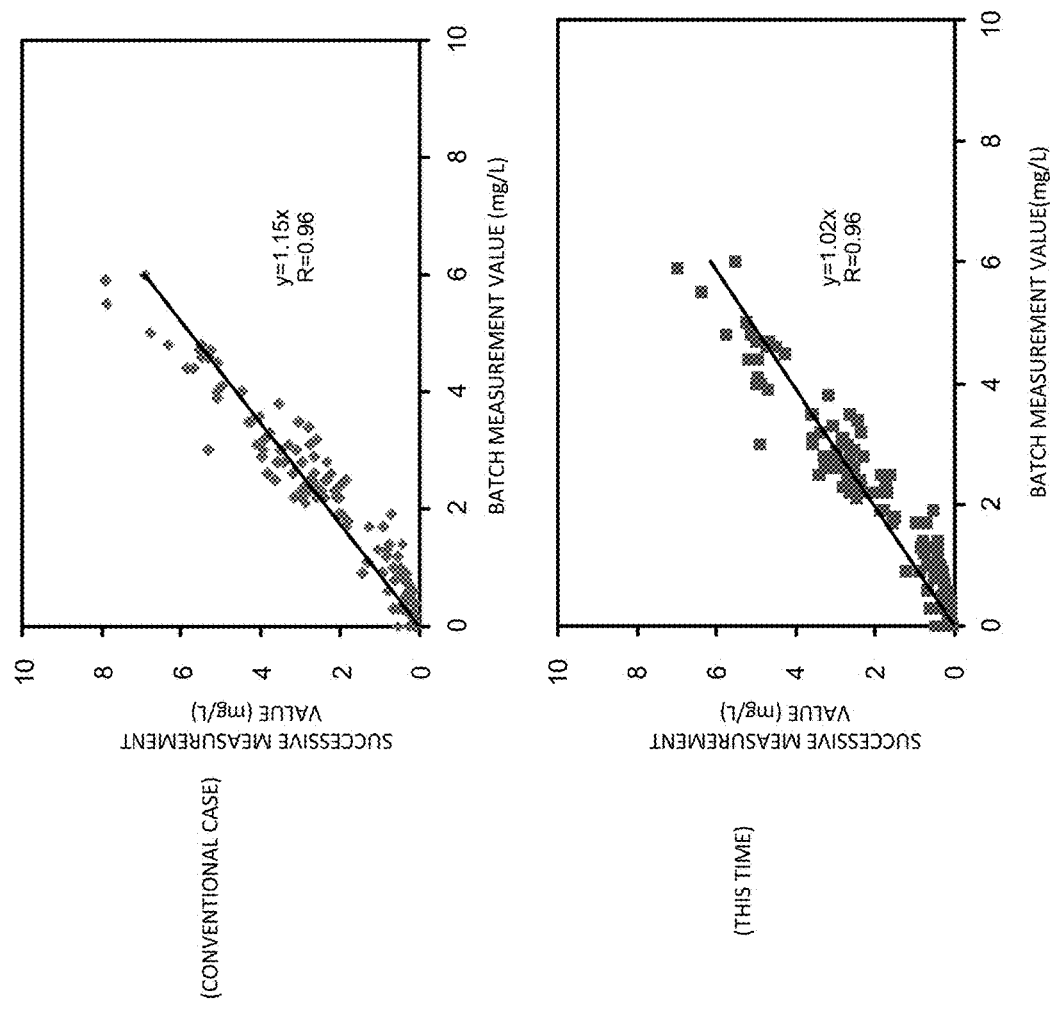
FIG. 5 is a graph illustrating the result of the comparison between the concentration measurement system in the same embodiment and a conventional system.

Here, the result of the comparison between a conventional case and the present embodiment is illustrated in FIG. 5.

In the conventional case, only on the low concentration side, matching of successive measurement values is performed, and as a result, as illustrated in the upper part of FIG. 5, when representing the correlation between a successive measurement value and a batch measurement value using a regression line, a slope (a regression coefficient) of 1.15, and a correlation coefficient R of 0.96 are obtained.

On the other hand, the concentration measurement system 100 according to the present embodiment matches a successive measurement value with a batch measurement value on any of the low concentration side and the high concentration side, and as a result, as illustrated in the lower part of FIG. 5, when representing the correlation between a successive measurement value and a batch measurement value using a regression line, a slope (a regression coefficient) of 1.02, and a correlation coefficient R of 0.96 are obtained.

As described above, although between the conventional case and the present embodiment, there is no difference in the correlation coefficient R, the slope in the present embodiment is closer to 1 than that in the conventional case, and it can be realized that successive measurement values were able to be measured with high accuracy without doubt.

Also, when measuring the concentration of a target component in a sample liquid where a biological reaction occurs as in the present embodiment, the concentration of ammonium ions fluctuates up and down due to some cause such as the activity of microorganisms, and therefore an appropriate correlation value varies time-dependently. On the other hand, in the concentration measurement system 100 according to the present embodiment, since the correlation value calculation part 25 successively calculates a correlation value when the second reception part 23 receives a batch measurement value in the latest batch measurement, and the ammonia nitrogen meter 10 uses the latest correlation value to calculate the concentration of ammonium ions, an appropriate correlation value can be used on a time-dependent basis.

Further, since the correlation value calculation part 25 calculates a correlation value on the basis of multiple successive measurement values and multiple batch measurement values, when accurately matching a successive measurement value with a batch measurement value, an appropriate value can be obtained as a correlation value.

In addition, since the information processing device 20 calculates a correlation value and transmits the correlation value to the ammonia nitrogen meter 10, for example, a user just inputs a batch measurement value to the information processing device 20, and can thereby make the ammonia nitrogen meter 10 automatically calculate concentration using the latest correlation value.

Second Embodiment

Next, a second embodiment of the concentration measurement system according to the present invention will be described.

A concentration measurement system according to the second embodiment is contrived in consideration of the problem that when the numbers of successive measurement values and batch measurement values obtained respectively using the first measurement device and the second measurement device are small, such as immediately after the start of system operation or immediately after calibration, a correlation expression or correlation value indicating the correlation between successive measurement values and corresponding batch measurement values cannot be accurately obtained.

Figure 6B:
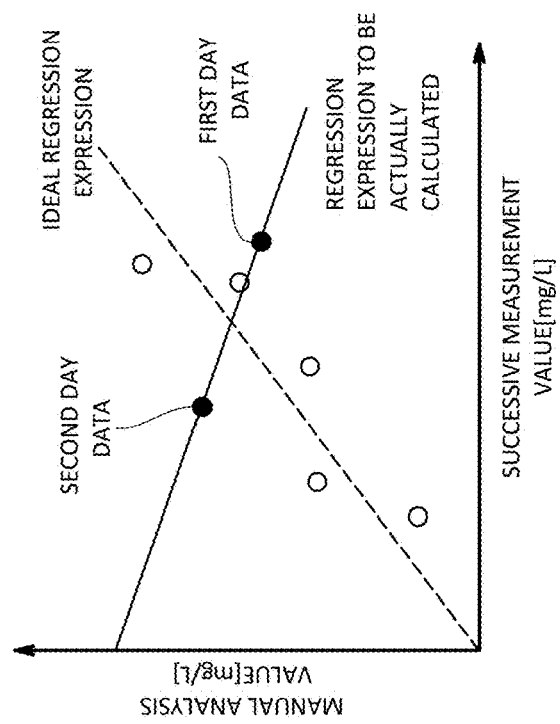
FIGS. 6(A) and 6(B) are diagrams for explaining the problem of a concentration measurement system in a second embodiment.
Figure 6A:
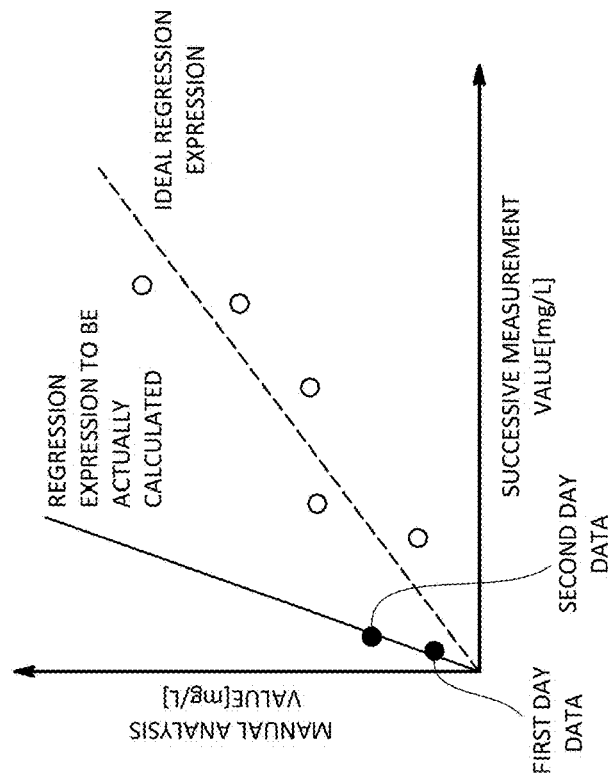

Describing this in more detail, an ideal correlation expression (e.g., a regression expression (regression model)) obtained when the number of data points respectively given by batch measurement values and successive measurement values corresponding to the batch measurement values is sufficiently prepared is assumed to be represented by a straight line given by a dashed line in FIG. 6A or 6B.

On the other hand, consider the case where the number of data points respectively given by batch measurement values and successive measurement values corresponding to the batch measurement values is small, and for example, only two, i.e., a first day data point and a second day data point. In this case, depending on the values of the actually obtained two points, a correlation expression (e.g., a regression expression) actually obtained on the basis of the two points is represented by a straight line given by a solid line in FIG. 6A or 6B. The actual correlation expression in FIG. 6A or 6B has a large difference in slope or has a reverse slope as compared with the ideal correlation expression, and the use of such an actual correlation expression causes the deterioration of measurement accuracy.

Accordingly, in order to make it possible to accurately obtain a correlation expression or a correlation value even when the number of data points respectively given by successive measurement values and corresponding batch measurement values is small, such as immediately after the start of system operation or immediately after calibration, the concentration measurement system according to the present embodiment is contrived.

In addition, in order to solve the above-described problem, the concentration measurement system according to the present embodiment is configured such that a correlation value calculation part calculates a correlation value using a preliminarily inputted temporary batch measurement value and a temporary successive measurement value preliminarily inputted as a successive measurement value corresponding to the temporary batch measurement value.

Figure 7:
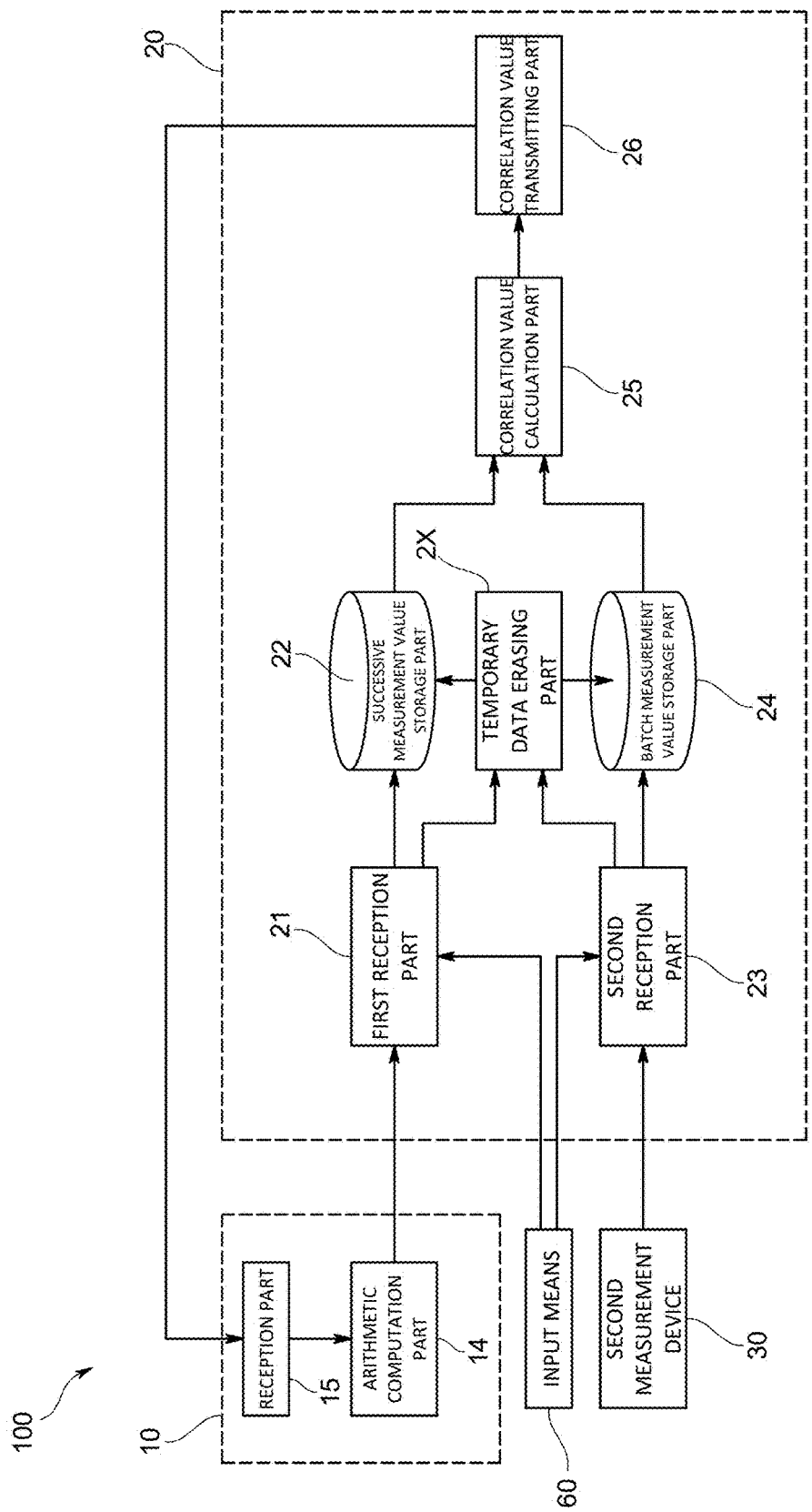
FIG. 7 is a functional block diagram illustrating the functions of an information processing device in the same embodiment.

Describing this more specifically, as illustrated in FIG. 7, an information processing device 20 in the present embodiment is configured such that a user can input the temporary batch measurement value and the temporary successive measurement value using input means 60 such as a keyboard. In addition, the externally inputted temporary successive measurement value is received by a first reception part 21 and stored in a successive measurement value storage part 22, and the externally inputted temporary batch measurement value is received by a second reception part 23 and stored in a batch measurement value storage part 24.

In the present embodiment, mutually corresponding multiple temporary successive measurement values and multiple temporary batch measurement values are preliminarily inputted and stored, and specifically, as the temporary successive measurement values and the temporary batch measurement values, values based on measurement values obtained in the past such as before system operation or before calibration are used.

The temporary successive measurement values and the temporary batch measurement values in the present embodiment are set to form combinations of x and y that, given that a temporary successive measurement value is x and a corresponding temporary batch measurement value is y, meets a predetermined relational expression. More specifically, it is adapted to set the maximum, minimum, and average values obtained by multiple times of past batch measurement respectively as the temporary batch measurement values y and values equal to the maximum, minimum, and average values respectively as the temporary successive measurement values x, and meet the relational expression "temporary batch measurement value y=corresponding temporary successive measurement value x".

Figure 8:
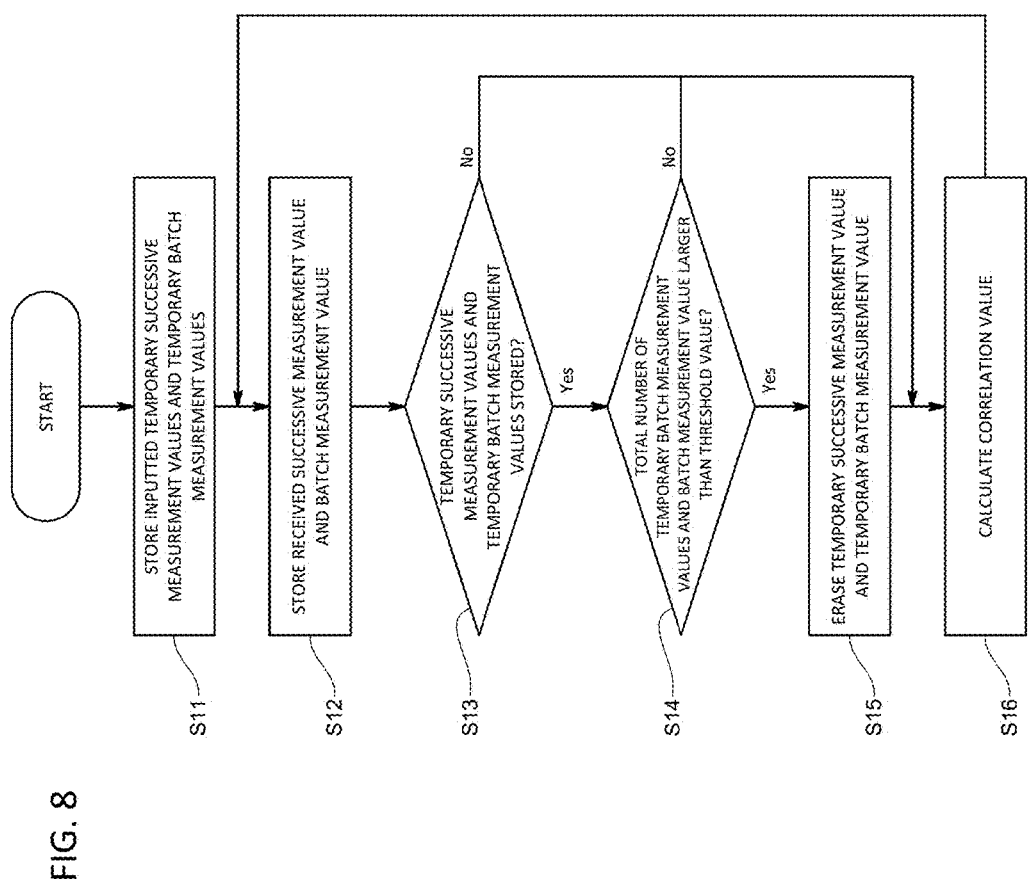
FIG. 8 is a flowchart illustrating the actions of the concentration measurement system in the same embodiment.

Next, the procedure for obtaining a correction value using the above-described temporary successive measurement values and temporary batch measurement values will be described with reference to a flowchart in FIG. 8.

First, the successive measurement value storage part 22 and the batch measurement value storage part 24 respectively store the temporary successive measurement values and the temporary batch measurement values inputted by, for example, a user before system operation or on another occasion (S11).

Then, when successive measurement by an ammonia nitrogen meter 10 as a first measurement device is started in the same manner as that in the first embodiment, the first reception part 21 receives a successive measurement value and the successive measurement value storage part 22 stores the value. On the other hand, when a batch measurement value obtained in batch measurement by a second measurement device 30 is inputted to the information processing device 20, the second reception part 23 receives the batch measurement value and the batch measurement value storage part 24 stores the value (S12), Note that as illustrated in FIG. 7, the information processing device 20 in the present embodiment further includes a temporary data erasing part 2X adapted to, after the successive measurement value and the batch measurement value have been inputted in S12, erase the temporary successive measurement values and the temporary batch measurement values from the successive measurement value storage part 22 and the batch measurement value storage part 24, respectively.

Specifically, after the successive measurement value and the batch measurement value have been inputted in S12, the temporary data erasing part 2X checks whether or not the temporary successive measurement values and the temporary batch measurement values are stored in the successive measurement value storage part 22 and the batch measurement storage part 24, respectively (S13).

When the temporary successive measurement values and the temporary batch measurement values are stored, the total number of the temporary batch measurement values and the batch measurement value stored in the batch measurement value storage part 24 is compared with a predetermined threshold value (S14).

Figure 9:
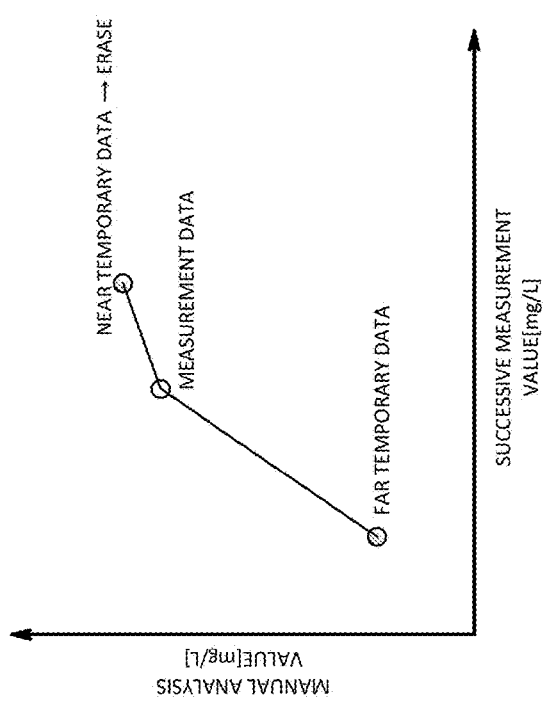
FIG. 9 is a diagram for explaining a temporary data erasing part in the same embodiment.

As a result of the comparison, when the total number is larger than the threshold value (i.e., when the number of data points are sufficiently prepared), the temporary data erasing part 2X erases the temporary successive measurement values and the temporary batch measurement values from the successive measurement value storage part 22 and from the batch measurement value storage part 24 one by one, respectively (S15). Specifically, as illustrated in FIG. 9, a point (a measurement data) given by the successive measurement value and the batch measurement value inputted in S12 is plotted in a graph with one axis as a successive measurement value and the other axis as a batch measurement value, and a temporary successive measurement value and temporary batch measurement value giving a point (temporary data) nearest to that point (measurement data) are erased. After that, the temporary data erasing part 2X transmits a calculation signal to the correlation value calculation part 25.

On the other hand, when the temporary successive measurement values and the temporary batch measurement values are not stored in S13, or when the total number of the temporary batch measurement values and the batch measurement value is smaller than the threshold value in S14 (i.e., when the number of data points is insufficient), the temporary data erasing part 2X transmits the calculation signal to the correlation value calculation part 25 without erasing any of the temporary successive measurement values and the temporary batch measurement values.

Upon receipt of the calculation signal, the correlation value calculation part 25 acquires two or the three temporary successive measurement values and the successive measurement value stored in the successive measurement value storage part 22 and two or the three batch measurement values and the batch measurement value stored in the batch measurement storage part 24, and uses the acquired values to calculate a correlation value (S16).

Figure 10:
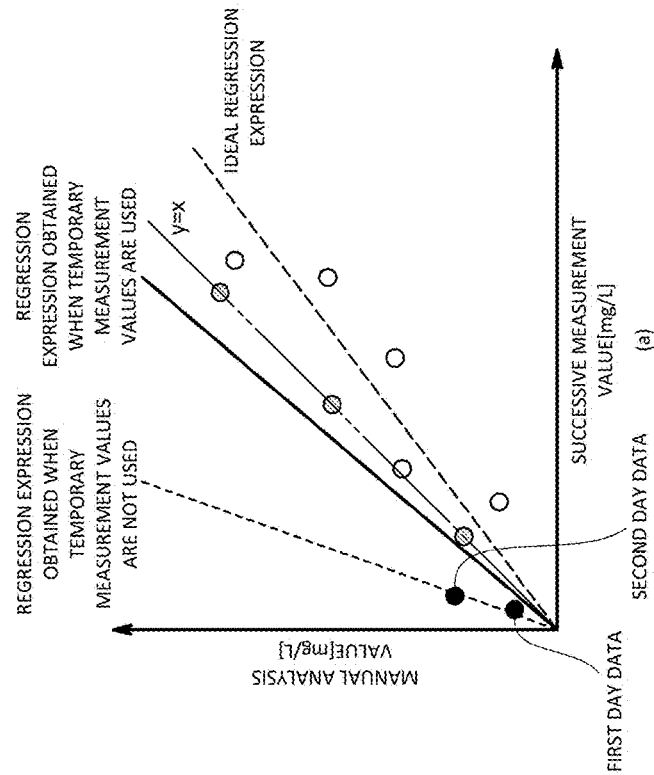
FIG. 10 is a diagram for explaining a correlation value calculation part in the same embodiment.

Specifically, as illustrated in FIG. 10, the correlation value calculation part 25 calculate, for example, a regression line using the temporary successive measurement values, successive measurement value, temporary batch measurement values, and batch measurement value, and obtains a regression coefficient of the regression line as the correlation value.

Note that when the above-described temporary data erasing part 2X has already erased all of the temporary successive measurement value and the temporary batch measurement value, the correlation value calculation part 25 calculates the correlation value on the basis of batch measurement values and corresponding successive measurement values in the same manner as in the first embodiment without using the temporary values.

Subsequently, S12 to S16 are repeated to calculate a correlation value, and the calculated correlation value is transmitted to the ammonia nitrogen meter 10 as the first measurement device or the calculated correlation value is used to correct a successive measurement value.

Figure 11A:
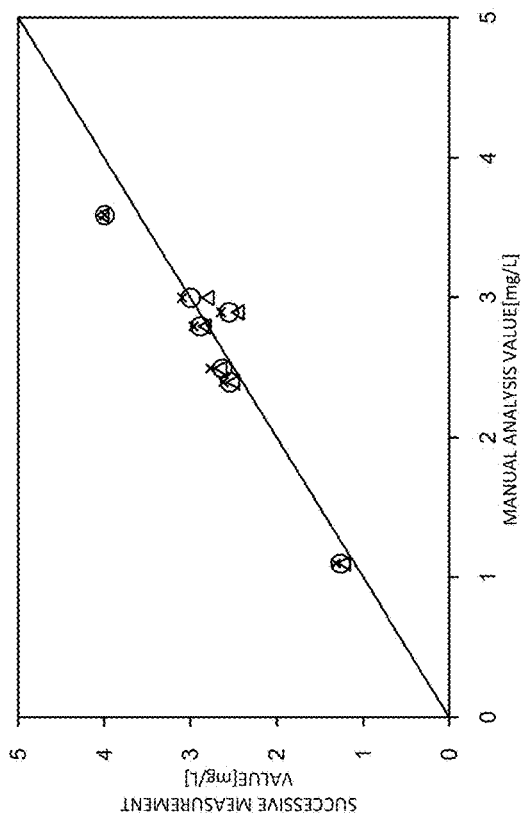
FIGS. 11(A) and 11(B) are graphs illustrating the result of the comparison between the concentration measurement system in the same embodiment and a conventional system.
Figure 11B:
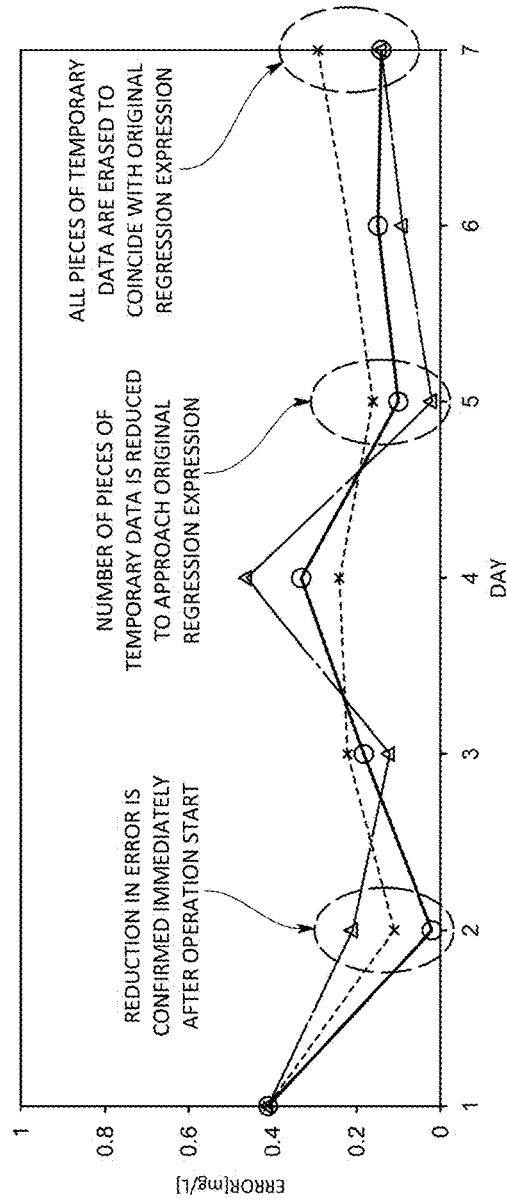

FIGS. 11(A) and 11(B) illustrate the result of comparing the case where the correlation value is calculated using the temporary successive measurement values and the temporary batch measurement values as described above and the case where a correlation value is calculated without using any of the temporary successive measurement values and the temporary batch measurement values. In addition, the case where no successive measurement value is corrected is also compared.

Here, as a comparative experiment, as illustrated in FIG. 12, the case where the temporary batch measurement values and the temporary successive measurement values corresponding to the temporary batch measurement values (a combination of a temporary batch measurement value and a temporary successive measurement value corresponding to the temporary batch measurement value is referred to as temporary data) are preliminarily inputted three by three and stored will be described. In addition, the above-described predetermined threshold value in S14 is set to 7, and until the fourth day, the three pieces of preliminarily inputted temporary data are used to calculate a correlation value, whereas after the fifth day, the three pieces of temporary data are erased one by one. Of course, the number of pieces of preliminarily inputted temporary data and the threshold value in S14 may be appropriately changed.

A circle "o" in the graphs of FIGS. 11(A) and 11(B) are plotted points that is given by a batch measurement value and a corrected successive measurement value corresponding to the batch measurement value obtained when a correlation value is calculated using at least one piece of temporary data and a successive measurement data is corrected using the correlation value under the above-described condition.

On the other hand, a triangle "Δ" in the graphs of FIGS. 11(A) and 11(B) are plotted points that is given by a batch measurement value and a corrected successive measurement value corresponding to the batch measurement value obtained when a correlation value is calculated without using any temporary data and a successive measurement value is corrected using the correlation value. Also, a cross "x" in the graphs of FIGS. 11(A) and 11(B) are plotted points that is given by a batch measurement value and a successive measurement value corresponding to the batch measurement value obtained without correcting the successive measurement value.

As a result of the above-described comparative experiment, it can be found that as listed in Table 1, in the case where a correlation value is calculated using at least one piece of temporary data, and a successive measurement value is corrected using the correlation value, an average error value and the total value of errors are 0.19 and 1.33, respectively, and a successive measurement value is accurately obtained as compared with the case where any temporary data is not used or the case where a successive measurement value is not corrected.

TABLE 1

| | Average error value | Sum of errors |
|---|---|---|
| No correction for 7 days | 0.24 | 1.65 |
| Correction without temporary data for 7 days | 0.21 | 1.45 |
| Correction with temporary data for 7 days | 0.19 | 1.33 |

As described above, the concentration measurement system 100 according to the present embodiment can accurately calculate a correlation value and highly accurately obtain a successive measurement value even when the number of data points respectively given by successive measurement values and corresponding batch measurement values is small, such as immediately after the start of system operation or immediately after calibration.

Further, the concentration measurement system 100 according to the present embodiment performs the regression using the temporary successive measurement values and the temporary batch measurement values, and correspondingly the number of measurement data points necessary to stabilize the regression can be reduced as compared with the case where the temporary successive measurement values and the temporary batch measurement values are not used.

In doing so, the regression can be performed using the latest measurement data, and therefore the regression expression and/or correlation value more suitable for a sensor condition of the moment can be calculated.

Note that the present invention is not limited to the any of the above-described first and second embodiments.

Figure 13:
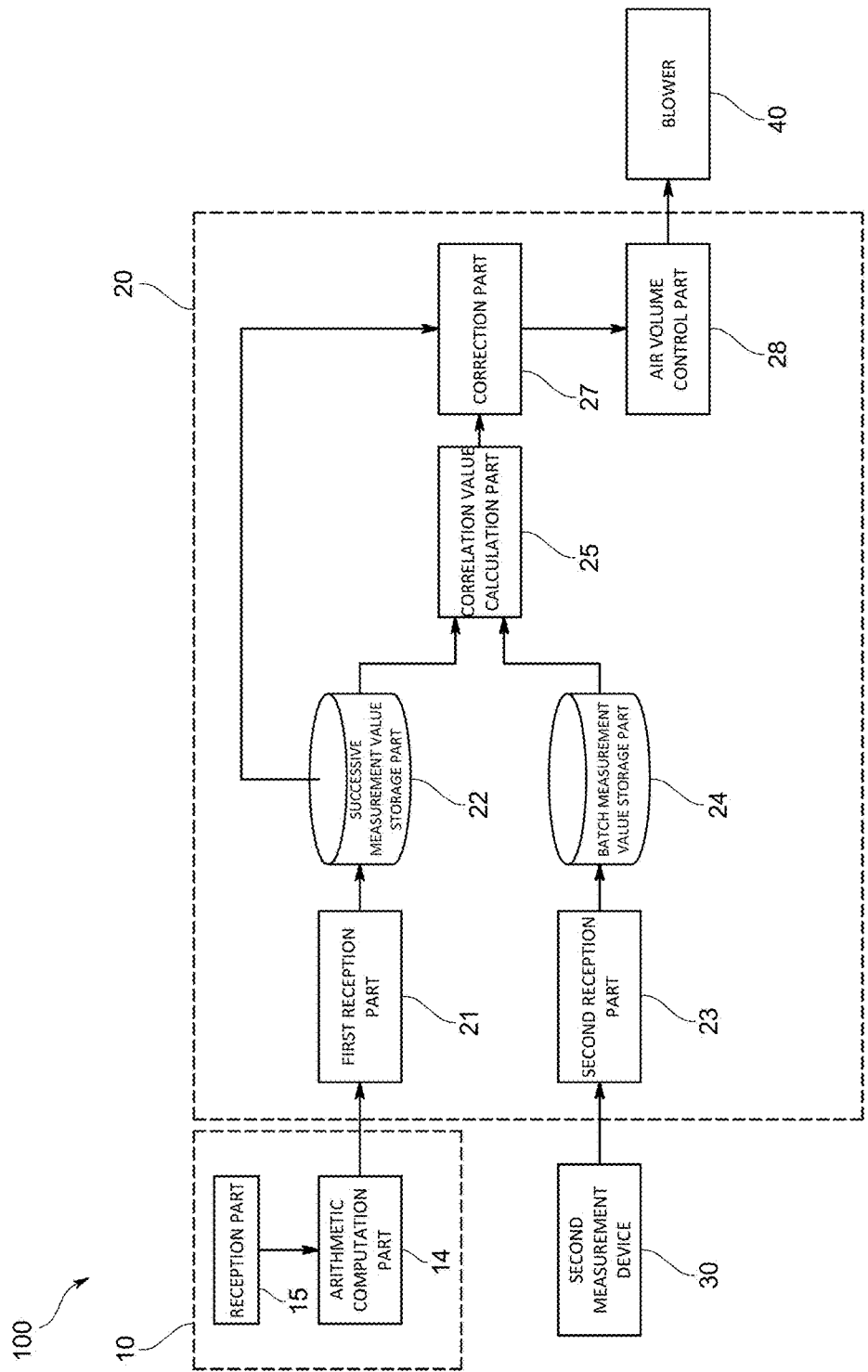
FIG. 13 is a functional block diagram illustrating the functions of an information processing device in a variation.

For example, in the first embodiment, the ammonia nitrogen meter 10 is configured to calculate the concentration of ammonium ions using a correlation value; however, as illustrated in FIG. 13, the information processing device 20 may be configured to correct a successive measurement value using a correlation value. Specifically, the information processing device 20 includes a correction part 27 adapted to acquire a successive measurement value received by the first reception part 21 and a correlation value calculated by the correlation value calculation part 25 as well as correcting the successive measurement value using the correlation value.

Also, as illustrated in FIG. 13, the information processing device 20 may further include a function as an air volume control part 28. Specifically, the air volume control part 28 acquires the successive measurement value corrected by the above-described correction part 27 as well as on the basis of the value, outputting an ON/OFF signal or an air volume control signal to the blower 40.

Figure 14:
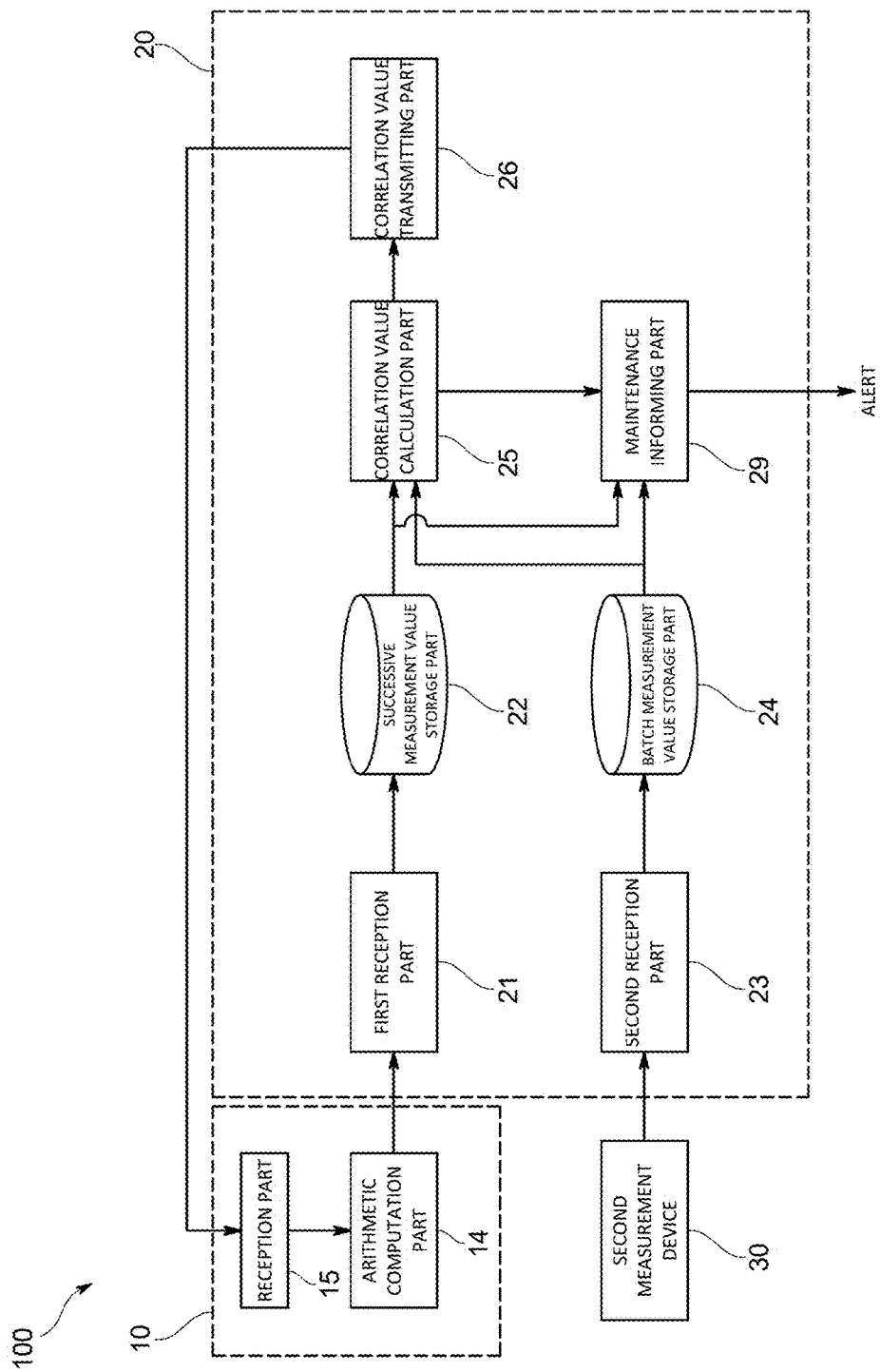
FIG. 14 is a functional block diagram illustrating the functions of an information processing device in another variation.

Further, as illustrated in FIG. 14, the information processing device 20 may further include a maintenance informing part 29 adapted to output an informing signal that informs that maintenance of the ammonia nitrogen meter 10 is required or the time for the maintenance is approaching.

The maintenance informing part 29 acquires a successive measurement value, a batch measurement value, and a correlation value calculated by the correlation value calculation part 25 as well as determining the time for the maintenance on the basis of these values. More specifically, the maintenance informing part 29 is adapted to issue an alert when the deviation between the successive measurement value and the batch measurement value reaches a predetermined value or more, or the correlation value reaches a predetermined value or more or a predetermined value or less.

Note that the maintenance informing part 29 may be adapted to acquire any one of a set of the successive measurement value and the batch measurement value, and the correlation value, and determine the time for the maintenance on the basis of the resulting value.

Meanwhile, when the concentration of a target component in a liquid reduces, suspended substances (SS) are reduced and suspended in the liquid, and as a result of demanding a target for a biological reaction, may be attached to the sensor parts S and/or the like of the ammonia nitrogen meter 10, and/or decompose a plasticizer inside the sensors. Accordingly, when the suspended substances in the liquid are reduced, the life of the ammonium electrode 11 or the like may be shortened.

Such a phenomenon affecting the life of an electrode may occur, for example, when the value of oxidation-reduction potential (ORP) or a dissolved oxygen amount (DO) is high, under the condition that the activity of microorganisms is high (e.g., the temperature of the liquid is 30° C. to 40° C.), and/or in other cases.

Figure 15:
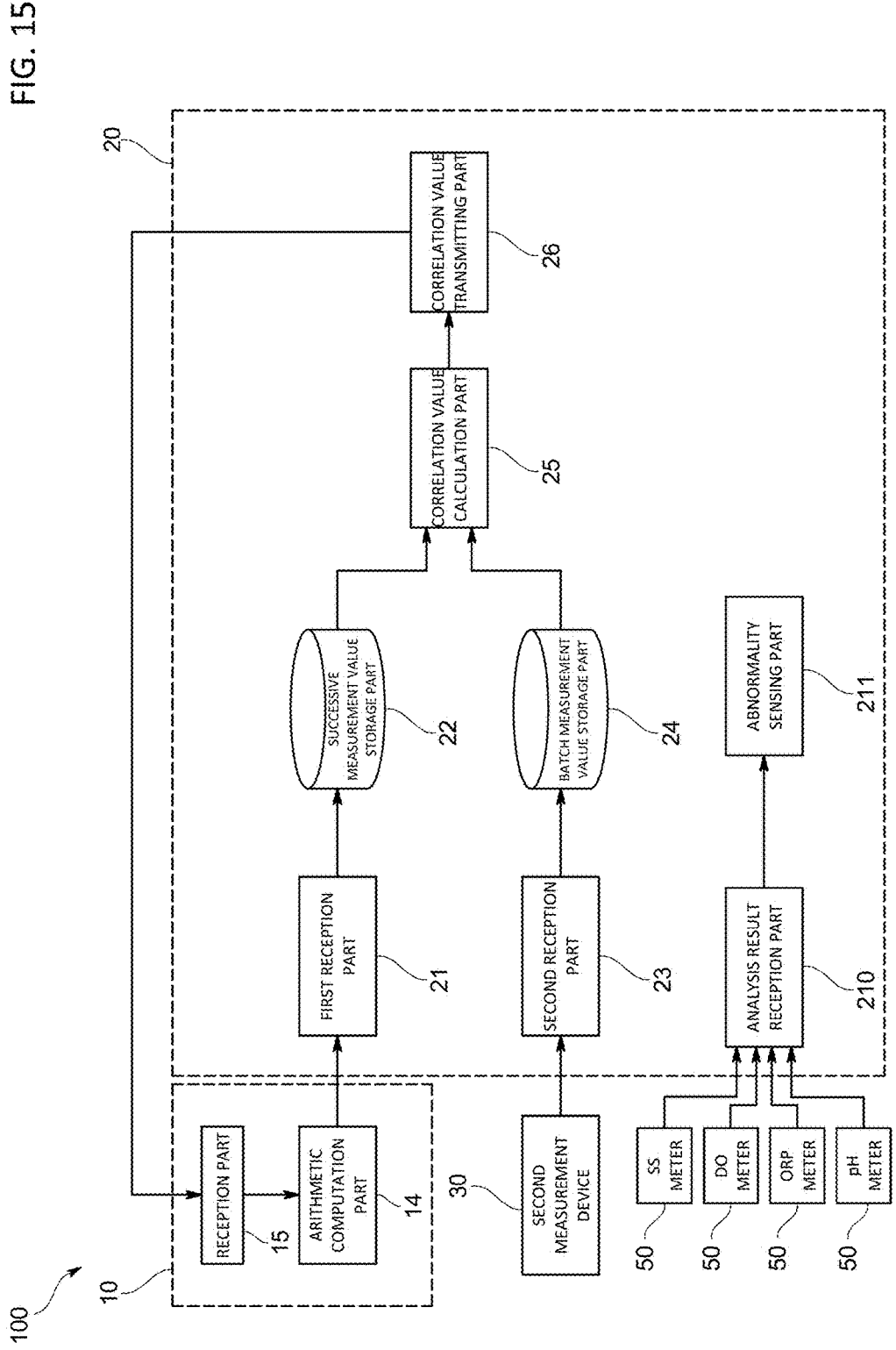
FIG. 15 is a functional block diagram illustrating the functions of an information processing device in still another variation.

For this reason, as illustrated in FIG. 15, the information processing device 20 may have: an analysis result reception part 210 adapted to receive analysis results from various different analyzers 50 (such as an SS meter, DO meter, ORP meter, and pH meter) for analyzing the amount of suspended substances (SS) and the amount of dissolved oxygen (DO) in the liquid subjected to the biological reaction process, ORP and pH of the liquid, and the like; and an abnormality sensing part 211 adapted to sense the abnormality of the ammonia nitrogen meter 10 on the basis of the analysis results.

Note that the various analyzers 50 may be ones included in the concentration measurement system 100 or ones separately provided to the biological reactors T or the like. In order to receive the analysis results from the analyzers 50 preliminarily provided separately from the concentration measurement system 100, it is preferable that the analysis result reception part 210 is configured to be able to receive the analysis results stored in, for example, a cloud.

In addition, part or all of the functions of the information processing device 20 in each of the above-described embodiments may be included in the ammonia nitrogen meter 10.

Figure 16:
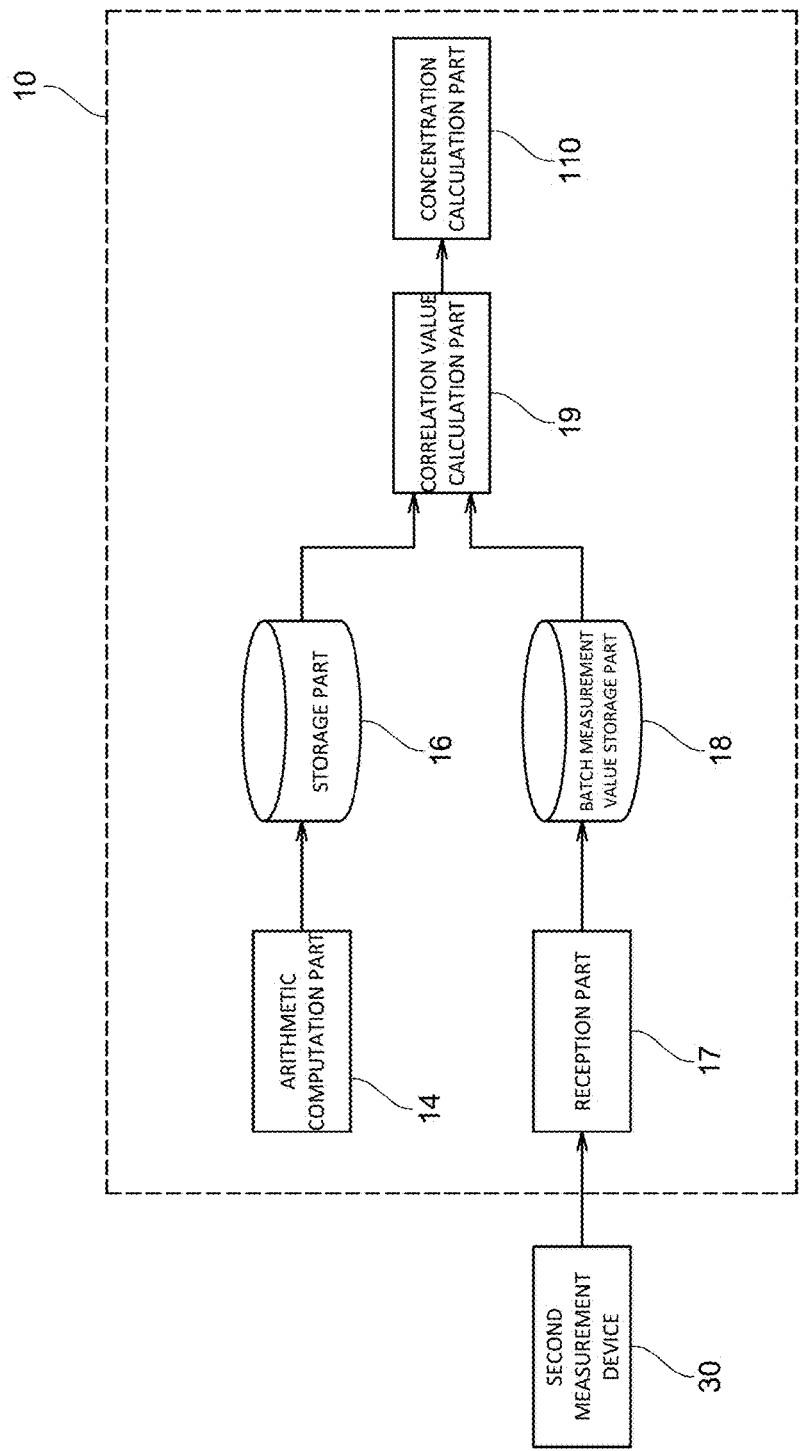
FIG. 16 is a functional block diagram illustrating the functions of an ammonia nitrogen meter in yet another variation.

Specific embodiments of such an ammonia nitrogen meter 10 include a configuration including: as illustrated in FIG. 16, an arithmetic computation part 14 adapted to successively compute the uncorrected concentration of ammonium ions on the basis of the potential difference between the ammonium ion electrode and the reference electrode; a storage part 16 adapted to store a successive measurement value obtained by the arithmetic computation part 14; a reception part 17 adapted to receive a batch measurement value obtained by performing batch measurement of the concentration of ammonium ions contained in the liquid sampled from the biological reactor T; a batch measurement storage part 18 adapted to store the batch measurement value; a correlation value calculation part 19 adapted to calculate a correlation value indicating the correlation between a successive measurement value and a batch measurement value; and a concentration calculation part 110 adapted to correct the uncorrected concentration of ammonium ions using the correlation value and thereby calculate the corrected concentration of ammonium ions.

In addition, mutually corresponding successive measurement and batch measurement are not limited to the definition in each of the above-described embodiments. For example, the successive measurement and the batch measurement may be such that the time difference between sampling time when the sample liquid was sampled from the biological reactor in the batch measurement and measurement time in the successive measurement is within a predetermined time during which the concentration of the target component in the liquid subjected to the biological reaction process does not substantially vary.

Also, in the above-described first embodiment, the batch measurement value storage part 24 stores a batch measurement value and sampling time in connection with each other. However, the batch measurement value storage part 24 may store a batch measurement value and time when corresponding batch measurement was performed in connection with each other, or store a batch measurement value and time when the second reception part 23 received the batch measurement value in connection with each other.

Further, the first measurement device is not limited to the ammonia nitrogen meter but may be a nitric acid meter having, for example, a chloride ion electrode and the like.

In addition, the first measurement device may be one adapted to, for example, in order to know the concentration of ammonia nitrogen in the biological reactor, measure potassium ion concentration, for example, that increases/decreases depending on the concentration of the ammonia nitrogen.

Besides, the first measurement device may be one having a sodium ion electrode, potassium ion electrode, calcium ion electrode, magnesium ion electrode, chloride ion electrode, bromide ion electrode, iodide ion electrode, sulfide ion electrode, copper ion electrode, cadmium ion electrode, lead ion electrode, or the like.

Additionally describing interfering ions acting when using the above-described first measurement device, for the sodium ion electrode, potassium ions, lithium ions, and/or ammonium ions act as the interfering ions; for the potassium ion electrode, cesium ions act as the interfering ions; for the calcium ion electrode, iron ions and/or zinc ions act as the interfering ions; for the copper ion electrode, iron ions act as the interfering ions; for the cadmium ion electrode, lead ions and/or iron ions act as the interfering ions; and for the lead ion electrode, iron ions, chromium ions, and/or cadmium ions act as the interfering ions.

Also, in the above-described second embodiment, the configuration in which the temporary data erasing part erases the temporary successive measurement values and the temporary batch measurement values is described; however, without erasing the externally inputted temporary successive measurement values and temporary batch measurement values, the temporary values may be used to calculate a correlation value even after the number of data points has been sufficiently prepared.

Further, in the above-described second embodiment, the maximum, minimum, and average values obtained by multiple times of past batch measurement are set as the temporary batch measurement value; however, this is only to allow a user to easily determine values to be inputted. The temporary batch measurement values may be appropriately changed, and the number of values to be inputted is also not limited to three.

In addition, in the above-described second embodiment, the temporary successive measurement values and the temporary batch measurement value are set so as to meet "temporary batch measurement value=corresponding temporary successive measurement value x"; however, the temporary successive measurement values and the temporary batch measurement values may be set so as to meet a function expression different from the relational expression above.

Also, without using the relational expression, batch measurement values actually obtained in the past (e.g., before calibration) and successive measurement values corresponding to the batch measurement values may be set as the temporary batch measurement values and the temporary successive measurement values, respectively. In this case, it may be adapted to determine whether or not any of the successive measurement values corresponding to the batch measurement values is an abnormal value (an outlier), and then when any of the successive measurement values is an abnormal value, select a likely successive measurement value other than the abnormal successive measurement value.

Besides, it goes without saying that the present invention is not limited to any of the above-described embodiments and variations, but can be variously modified without departing from the scope thereof.

DESCRIPTION OF REFERENCE CHARACTERS

100: Concentration measurement system
T: Biological reactor
10: Ammonia nitrogen meter
20: Information processing device
21: First reception part
22: Successive measurement value storage part
23: Second reception part
24: Batch measurement value storage part
25: Correlation value calculation part
26: Correlation value transmitting part

The invention claimed is:

1. A concentration measurement method for measuring target component concentration in a liquid, the method comprising:
   a first reception step of receiving a successive measurement value obtained by performing successive measurement of the target component concentration with use of a first measurement device of which a sensor part is immersed in the liquid;
   a second reception step of receiving a batch measurement value obtained by performing batch measurement of the target component concentration in a part sampled from the liquid, with use of a second measurement device different from the first measurement device; and
   a correlation expression calculation step of sequentially calculating, upon receipt of batch measurement value in the second reception step, a correlation expression indicating a correlation between multiple successive measurement values and multiple batch measurement values respectively obtained in mutually corresponding multiple times of successive measurement and multiple times of batch measurement, wherein
   the first measurement device calculates the target component concentration with use of the correlation expression or corrects the successive measurement value with use of the correlation expression; and
   the correlation expression includes a correlation value which is calculated during the correlation expression calculation step.

2. The concentration measurement method according to claim 1, further comprising:
a successive measurement value storage step of storing the successive measurement value received in the first reception step; and
a batch measurement value storage step of storing the batch measurement value received in the second reception step, wherein
in the correlation expression calculation step, the correlation expression is calculated on a basis of multiple batch measurement values, and respectively corresponding multiple successive measurement values, from among stored batch measurement values and stored successive measurement values, wherein
the multiple batch measurement values are selected from a predetermined number of batch measurement values that include the latest obtained batch measurement value and the batch measurement value immediately preceding the latest batch measurement value.

3. An apparatus comprising: a processor, and a memory storing software modules of a concentration measurement program used to measure target component concentration in a liquid, the software modules to be executed by the processor, the software modules comprising:
a first reception part adapted to receive a successive measurement value obtained by performing successive measurement of the target component concentration with use of a first measurement device of which a sensor part is immersed in the liquid;
a second reception part adapted to receive a batch measurement value obtained by performing batch measurement of the target component concentration in a part sampled from the liquid, with use of a second measurement device different from the first measurement device;
a correlation expression calculation part adapted to sequentially calculate, upon receipt of batch measurement value by the second reception part, a correlation expression indicating a correlation between multiple successive measurement values and multiple batch measurement values respectively obtained in mutually corresponding multiple times of successive measurement and multiple times of batch measurement, and
a correlation expression transmitting part adapted to transmit the correlation expression to the first measurement device or a correction part adapted to correct a successive measurement value received by the first reception part with use of the correlation expression.

4. A concentration measurement system that measures target component concentration in a liquid, the system comprising:
a first measurement device adapted to perform successive measurement of the target component concentration with a sensor part immersed in the liquid; and
an information processing device adapted to transmit and receive data with the first measurement device, wherein
the information processing device has:
a first reception part adapted to receive a successive measurement value obtained by performing successive measurement of the target component concentration with use of the first measurement device;
a second reception part adapted to receive a batch measurement value obtained by performing batch measurement of the target component concentration in a part sampled from the liquid, with use of a second measurement device different from the first measurement device;
a correlation expression calculation part adapted to sequentially calculate, upon receipt of batch measurement value by the second reception part, a correlation expression indicating a correlation between multiple successive measurement values and multiple batch measurement values respectively obtained in mutually corresponding multiple times of successive measurement and multiple times of batch measurement, the correlation expression including a correlation value which is calculated by the correlation expression calculation part; and
a correlation expression transmitting part adapted to transmit the correlation expression to the first measurement device or a correction part adapted to correct a successive measurement value received by the first reception part with use of the correlation expression.

5. The concentration measurement system according to claim 4, wherein
the information processing device has:
an analysis parameter reception part adapted to acquire an analysis parameter different from the target component concentration; and
an abnormality sensing part adapted to sense abnormality of the first measurement device on a basis of the analysis parameter.

6. The concentration measurement system according to claim 4, wherein
the information processing device further has a maintenance informing part adapted to acquire the correlation value, or the successive measurement value and the batch measurement value as well as on a basis of the correlation value, or the successive measurement values and the batch measurement values, outputting an informing signal prompting maintenance of the first measurement device.

7. The concentration measurement system according to claim 4, wherein
the correlation expression calculation part calculates the correlation expression with additional use of a preliminarily inputted temporary batch measurement value and a temporary successive measurement value preliminarily inputted as a successive measurement value corresponding to the temporary batch measurement value.

8. A concentration measurement device that performs successive measurement of target component concentration in a liquid with a sensor part immersed in the liquid, the concentration measurement device having:
a reception part adapted to receive a batch measurement value obtained by performing batch measurement of the target component concentration in a part sampled from the liquid, with use of a second measurement device different from the concentration measurement device;
a correlation expression calculation part adapted to sequentially calculate, upon receipt of batch measurement value by the reception part, a correlation expression indicating a correlation between multiple successive measurement values and multiple batch measurement values respectively obtained in mutually corresponding multiple times of successive measurement and multiple times of batch measurement; and
a concentration calculation part adapted to calculate the target component concentration with use of the correlation expression, wherein the correlation expression includes a correlation value which is calculated by the correlation expression calculation part.

* * * * *